US 6,658,939 B2

(12) United States Patent
Georgeson et al.

(10) Patent No.: US 6,658,939 B2
(45) Date of Patent: Dec. 9, 2003

(54) FIXTURE FOR AUTOMATED ULTRASONIC SCANNING OF RADII IN AEROSPACE STRUCTURE

(75) Inventors: Gary E. Georgeson, Federal Way, WA (US); Daniel J. Wright, Mercer Island, WA (US); Gary F. Dokken, Seattle, WA (US); Martin L. Freet, Federal Way, WA (US); Stanley W. Richardson, Bothell, WA (US)

(73) Assignee: The Boeing Company, Seattle, WA (US)

( * ) Notice: Subject to any disclaimer, the term of this patent is extended or adjusted under 35 U.S.C. 154(b) by 0 days.

(21) Appl. No.: 09/768,651

(22) Filed: Jan. 24, 2001

(65) Prior Publication Data

US 2002/0017140 A1 Feb. 14, 2002

Related U.S. Application Data

(60) Provisional application No. 60/178,582, filed on Jan. 28, 2000.

(51) Int. Cl.[7] .............................................. G01N 29/04
(52) U.S. Cl. ......................................... 73/621; 73/625
(58) Field of Search ........................ 73/621, 619, 634, 73/633, 622, 624, 628, 625, 640, 641, 632; 376/249, 250

(56) References Cited

U.S. PATENT DOCUMENTS

| | | | | |
|---|---|---|---|---|
| 3,882,717 A | | 5/1975 | McCauley | 73/67 |
| 4,043,185 A | * | 8/1977 | Siebert | 73/67.7 |
| 4,117,733 A | | 10/1978 | Gugel | 73/634 |
| 4,143,553 A | | 3/1979 | Martens et al. | 73/625 |
| 4,244,227 A | * | 1/1981 | Rudolph et al. | 73/621 |
| 4,487,071 A | | 12/1984 | Pagano et al. | 73/612 |
| 4,492,119 A | * | 1/1985 | Dulapa et al. | 73/621 |
| 4,526,037 A | | 7/1985 | Wentzell et al. | 73/640 |
| 4,532,808 A | | 8/1985 | Wentzell et al. | 73/640 |
| 4,612,808 A | | 9/1986 | McKirdy et al. | 73/622 |
| 4,807,476 A | | 2/1989 | Cook et al. | 73/620 |
| 4,848,159 A | | 7/1989 | Kennedy et al. | 73/641 |
| 4,881,177 A | * | 11/1989 | McClean et al. | 73/619 |
| 4,980,872 A | | 12/1990 | Oler et al. | 367/173 |
| 5,031,458 A | | 7/1991 | Young et al. | 73/636 |
| 5,203,869 A | | 4/1993 | Bashyam | 73/640 |
| 5,249,457 A | * | 10/1993 | Minichan | 73/105 |
| 5,586,155 A | * | 12/1996 | Erbes et al. | 376/249 |
| 6,220,099 B1 | * | 4/2001 | Marti et al. | 73/633 |

* cited by examiner

Primary Examiner—Hezron Williams
Assistant Examiner—Jacques Saint-Surin
(74) Attorney, Agent, or Firm—Conrad O. Gardner

(57) ABSTRACT

An ultrasonic scanner for inspection of radiused regions having scanner supports which include pivoted fingers containing the transducers and hands supporting the fingers attached to vertical arms by pins. The angle of the hands are controlled by the vertical position of the arms.

2 Claims, 4 Drawing Sheets

FIXTURE FOR AUTOMATED ULTRASONIC SCANNING OF RADII IN AEROSPACE STRUCTURE

CROSS-REFERENCE TO RELATED APPLICATIONS

This application is a conversion of provisional application Ser. No. 60/178,582, filed Jan. 28, 2000.

BACKGROUND OF THE INVENTION

1. Field of the Invention

This invention relates to ultrasonic scanning and more particularly to ultrasonic scanning of radii in composite structures.

2. Description of the Related Art

Composite structure designed for aerospace applications often contains radiused "I", "U" or "T" intersections. For design reasons, these intersections have some sort of external radius (ie., they do not have sharp corners), and contain an internal filer material of some sort, called a "noodle." The quality of the noodle, its interface with the composite plies, and the consolidation of the plies, are all critical to proper joint functioning. The quality of the intersection of webs and flanges in composite spars, or webs and skins in co-cured structure are critical to their performance. Flaws, such as cracks, voids, or delaminations can form in this region, and adversely affect the structure. However, these radiused regions are not easy to inspect well.

Up to this point, the inspection of radiused noodle regions of composite spars and co-cured structures has been a time-consuming, labor-intensive procedure that has shown questionable consistency. Timely, accurate, and reliable nondestructive characterization of these regions is very important, and is the problem this invention adresses.

Until now, inspection of radiused regions has done by hand using a UT transducer in pulse-echo mode with a radiused shoe mounted on its end. The operator holds the shoe against the inner radius of the part, sliding it along the length, and rocking it back and forth over a near 90° angle. He/she is looking for flaw indications that will reflect the ultrasound back to the transducer, to be picked up and indicated by changes in a amplitude/time trace on an oscilloscope. He must determine "on the fly" whether or not the UT reflection amplitude is high enough and (at the same time) the extent of the flaw is also great enough to disqualify the part. The inspector will utilize a radius flaw standard a pre-determined NDI criteria for flaw amplitude and length.

There are significant problems with this approach. First, it is costly and time consuming to inspect the radii by hand. It is slow work, and ties up an inspector the entire time. The rest of the structure is inspected in an automated fashion on a UT scanning system. Second, this method is operator dependent, and subject to potential errors. The operator must watch an oscilloscope, looking for signal changes, while moving the transducer in the radial and axial directions by hand. The flaw indications are often subtle, must be tracked at multiple angles, and complete coverage of the radii is sometimes difficult to ensure. Third, the existing method does not provide reviewable image data. No data is saved to be analyzed later, nor can it be reviewed if there are any questions. Fourth, the current method does not produce images that show the size or length of any indications that are found. The inspector simply marks the measured length of an indication on the part itself.

There are multiple transducer automated UT scanning systems that make use of multiple transducers in a variety of orientations. However, with the present invention, only a single transducer is needed at the radii, and costly multiple channel pulser/receiver systems are not required.

Patent Literature

U.S. Pat. No. 4,980,872 shows an ultrasonic probe coupled to an extension arm which can be mounted to a movable carriage. The angle of the probe can be manually controlled from the opposite end of the extension arm via a mechanical linkage. U.S. Pat. No. 4,807,476 describes an ultrasonic inspection system for inside radii comprised of a shoe having a single transducer. The signal is directed by two reflectors, one fixed which turns the signal 90 degrees and another that can be rotated and reflects the signal at 90 degrees again, but by rotation can cover all angles required to inspect the entire radius. The control system causes the probe to traverse the area in multiple passes while changing the angle at each pass to create a raster scan image. J U.S. Pat. No. 4,612,808 discloses a gimballed ultrasonic probe head with special gimbal geometry so that when used to inspect the junction 9 of a pipe with a cylinder, it will always keep the probe pointed toward the axis of the pipe. U.S. Pat. No. 4, 526,037 describes a mechanism for keeping two ultrasonic probes, one on either side of an outside corner, aligned as they are rotated around the saddle contour formed by the junction of an inlet nozzle and a reactor vessel. As part of the mechanism, the probes are pivotably mounted to either end of a rocker arm. U.S. Pat. No. 4,117,733 also describes a system for ultrasonic inspection of the junction of a nozzle with a pressure vessel. Ultrasonic transducers are pivotably mounted on arms which also pivot with respect to a central shaft to allow inspection at various radial distances from the central shaft.

Systems of the prior art for ultrasonic inspection of radii utilizing a number of transducers fixed at various angles and mounted to a carriage or machine can be contrasted to the present system where only a single transducer is needed at the radii.

BRIEF SUMMARY OF THE INVENTION

The present invention utilizes an opposed pair of water coupled ultrasonic transducer mounted in fingers with a suitable and radius to fit the fillet radius. The base of each finger is mounted to a hand and is free to rotate about an axis parallel to the longitudinal axis of the part to be inspected. The hands are mounted to arms via a three-position connection so they can be rapidly reconfigured for inspecting upper and lower radii and the webs of the parts. The arms are mounted at their upper ends by two vertically spaced bearings riding on shafts that project horizontally from a base structure. The arms are pulled toward one another by a rubber band stretched between them. The base structure couples the mechanism to a gantry robot. In operation the mechanism is moved into position so the fingers ride in the desired radii at a desired angle, and a longitudinal sweep is made to collect data. The vertical position of the sensor system is then changed slightly, which changes the angle of the fingers, and another longitudinal sweep is made. This is repeated until all desired angles are covered.

DETAILED DESCRIPTION OF THE INVENTION

Figure 1:
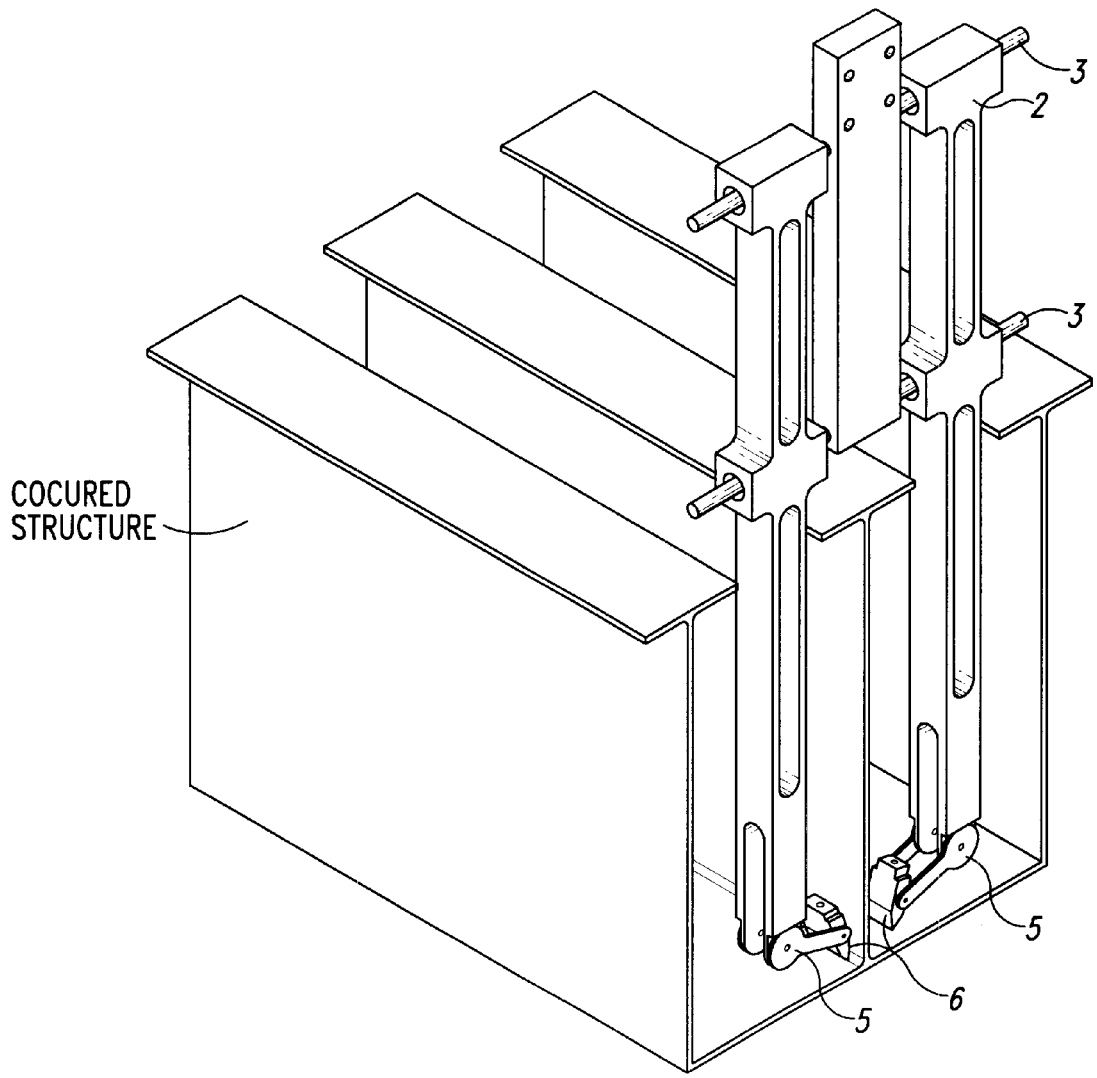
FIG. 1 is illustrative of a three dimensional model of the present ultrasonic scanning apparatus being readied to scan a 3-spar co-cured part.
Figure 2:
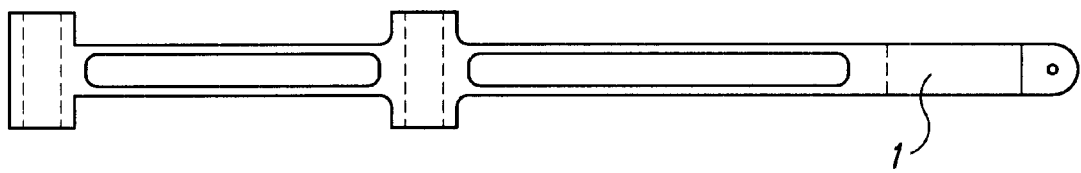
FIG. 2 is illustrative of one of the two aluminum arms utilized in the apparatus of FIG. 1.
Figure 3:
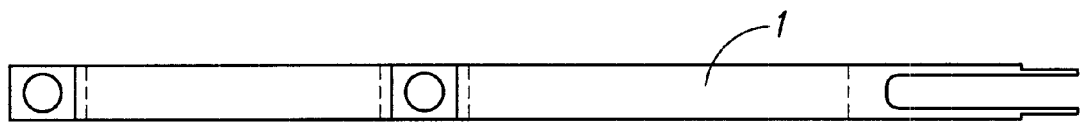
FIG. 3 is illustrative of one side of the hand (one of two for each hand) of the apparatus of FIG. 1, which connects the arm to an acrylic finger that rides the spar radius.
Figure 4:
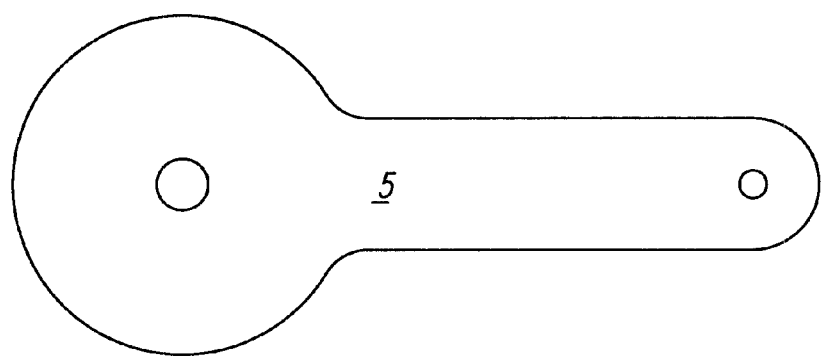
FIG. 4 is illustrative of a finger utilized in the preferred embodiment of the present invention.

The fixture is made up of two spring loaded "hands" that are attached by pins to "arms" that slide on sleeves to maintain relative orientation. FIG. 1 is a solid 3D model of the invention, along with a 3-spar co-cured structure. FIG. 2 is the design of the aluminum "arm" (one of two arms), which was designed to be both lightweight and resistant to bending. FIG. 3 shows the design of one side of a "hand" (one of two for each hand), which connects the "arm" to an acrylic "finger". Each "hand" holds a radiused "finger" that rides in the spar radius. A "finger" is shown in FIG. 4. A UT transducer is mounted inside each finger. Small plastic tubes are connected to small passageways (not shown) in the acrylic "fingers". Water is pumped through the tubes, into the passageways, and out in front of the transducers, to provide a good ultrasonic coupling medium between the transducer face and the part. The entire fixture is attached to the bridge of an automated UT scanning system which provides the electrical pulses to the transducers, as well as the controlled motion of the bridge. The angle of the "hands" must be controlled over a near 90° angle. This is done by automatic control of the vertical position of the scanning fixture. After each scan pass along the length of a spar, the scanning head raises (or lowers) a preset amount FIG. 1 is a 3-D model of invention being readied to scan a co-cured part rotating the "hands" a preset amount to a new angle-and another horizontal pass is made. This rotation using z-axis movement is a unique feature of the present invention.

The fixture can be easily set to inspect upper or lower web/cap or web/skin interfaces. The data is collected by the automated system, which provides reviewable image data. Hard copy UT amplitude and time-of-flight images are made, as is typically done for flat areas of a part under inspection. Full waveform UT data is saved, so it can be analyzed later, or reviewed if there are any questions about the results.

FIG. 2 is an "Arm" design; for lightweight stiffness, this part is made of aluminum.

FIG. 3 is a view of one side of the "hand" design; there are two of these each per "hand."

FIG. 4 is a view of the Acrylic "finger", which holds the UT transducer, and attaches to the "hand." A novel feature of this invention is that it allows automated UT data collection of radius inspections, using a single transducer for each radius, the angle of which is determined by z-axis head location. It does not require multiple transducers, nor the expense of multiple channel pulser/receiver and data acquisition and registration, to access the various angles required to do a proper scan. Nor does it require complicated or expensive mechanisms to change the angle of the transducers. It is inexpensive to fabricate, has few parts, and requires little or no maintenance. It allows UT scanning of straight spars and co-cured structure with a simple 2-axis bridge. Curved spars and co-cured structures can be scanned too, if the scanning system has the capability of being "taught" to follow the contours prior to scanning (as is the case with the scanner this fixture is used on). Once the scan system is "taught" the contour, z-axis incremental movements relative to the contour are programmed in to produce the proper "hand" (and, therefore, transducer) rotation.

Figure 5:
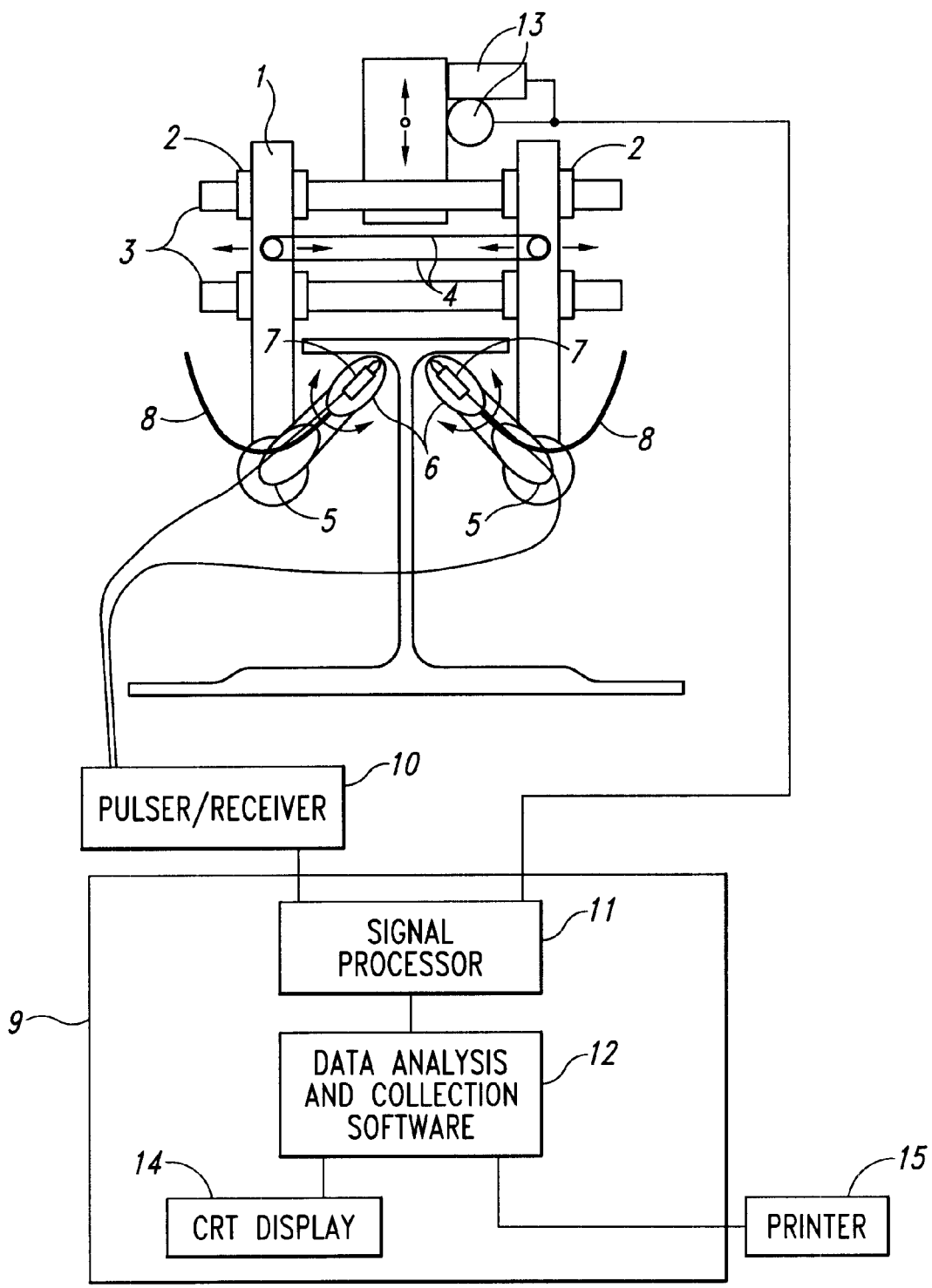
FIG. 5 is a block diagram of the present inspection system further including the present scanning apparatus.
Figure 6:
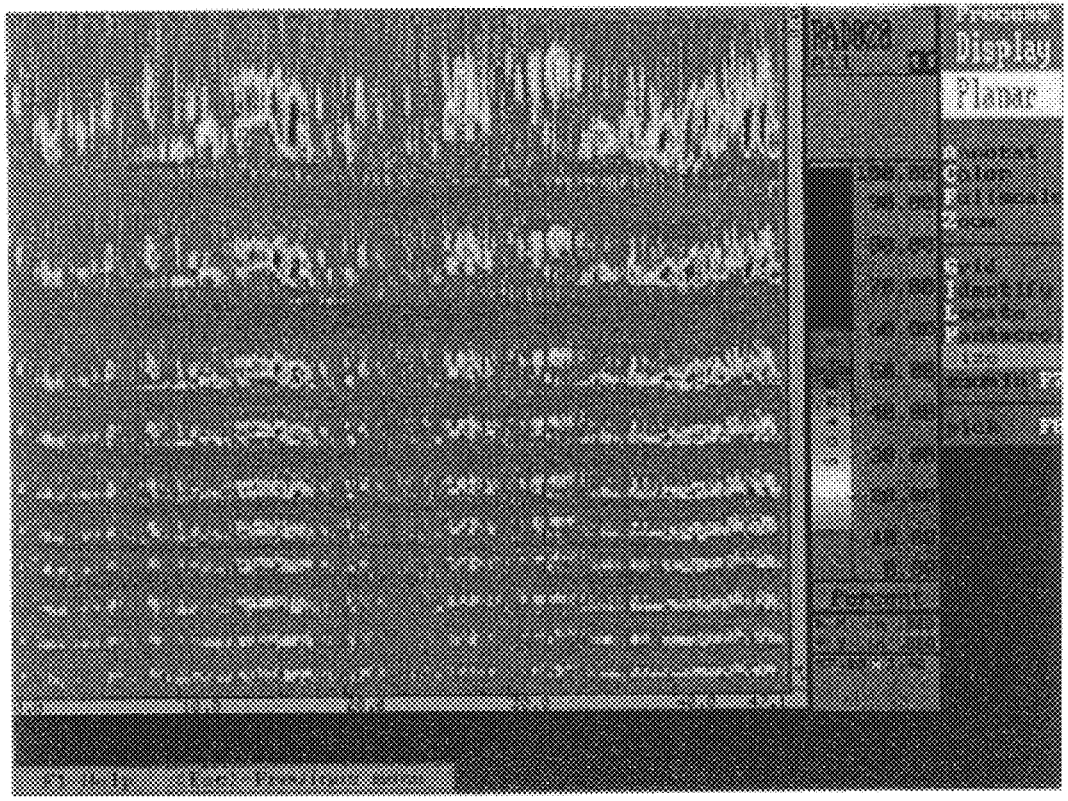
FIG. 6 is a graph of amplitude reflection data taken on one side of a cop-cured spar with flaws in the radius.
Figure 7:
FIG. 7 is illustrative of UT reflection amplitude results in the radius region showing flaws.

The invention has been designed, built, tested, and implemented for inspection of radii in I-beam spars and co-cured structure. FIG. 5 is a sketch of the assembly and block diagram of entire system. FIG. 6 is example of test data taken on a co-cured spar. In this case, the image resolution versus number of "hand" angles was being investigated. The reflected signal amplitude is shown as a function of location within the spar radius. The top data strip was made with 35 angles; the bottom, with 5 angles. The latter is seven times faster to generate than the former, but does not have the flaw resolution of the data strips above it. FIG. 7 shows UT reflection amplitude results from another scan taken over a two foot length of a co-cured spar.

FIG. 5 Diagram of Inspection System

The two "arms" (1) contain bushings (2) that slide on rods (3) which hold the assembly together. An elastic band (4) pulls the arms toward each other and holds them against the part to be inspected. The "hands" (5) are set at an appropriate angle for the particular part to be inspected. The "fingers" (6) which hold the ultrasonic transducers (7), are free to rotate. Their orientation is controlled by the vertical (z-axis) motion of the fixture relative to the part. Water flows through the hollow plastic tubes (8) and forms an ultrasonic couplant between the transducer heads and the part surface.

The transducers (7) are electrically connected to a computer-controlled ultrasonic test system (9). The test system contains a pulser/receiver module (10) that sends electric pulses that are transformed into mechanical pulses in face of the transducer. These mechanical pulses produce ultrasonic waves that travel into the part being inspected. Part of the waves can be reflected by flaws or features inside the part and will return to the transducer, which translates the ultrasonic waves into electrical pulses. These pulses are received by the pulser/receiver (10). A signal processor (11) translates the analog pulses into digital data that can be analyzed for amplitude and phase or time characteristics using data collection and analysis software (12). The 2 or 3 axis robot has positionally encoded motors (13) which produce the z and x axis scanning location relative to the part. The fixture translates the z-axis movement into the rotation of each "finger" (6). Computer software combines the returning pulse features (such as amplitude or time-of-flight) with the encoder position to produce 2-dimensional images of ultrasonic data that are evaluated on the CRT display (14). The images can also be produced in hard copy form using a printer (15). FIG. 6 is an example of an UT amplitude versus position scan, using various numbers of "finger" angles.

FIG. 6 UT reflection amplitude data taken on one side of a co-cured spar with flaws in the radius, using this invention. A 5 Mhz focused transducer was used. A range of 5 to 35 "finger" angles (produced by varying the z-axis step height) was taken to measure flaw detectability. At the chosen settings, red regions are indicate good areas and yellow, green and blue regions are higher reflections indicating flaws (The flaw indications show up as white (for yellow) and black (for green and blue) regions on black & white copies of this picture).

FIG. 7 UT reflection amplitude results in the radius region using invention. The dark (black) areas are flaws. The scale beneath the image is in inches.

The present invention has been shown to be a significant improvement over hand-held inspection. Once the system is set up for a scan, the operator is free to go work on something else. The inspector is provided with digital image data, and has much greater clarity on the configuration of the flaw indications than one obtains in the prior scope trace of hand-held inspection. The present system saves inspection time (50–75% faster, depending on the flaw resolution required) and significantly reduces touch-labor (by as much as 95%). It provides much better data for informed decision-making, reduces risk associated with inspection uncertainty, and eliminates the necessity to reinspect if questions about the result come up.

The present invention allows automated joint radius ultrasonic inspection using a simple 2 axis (x-z) or 3 axis (x-y-z) robotic manipulator. The device holds the transducers in proper positions and angles for inspection, and (by use of mechanically floating "arms" and rotating "fingers") translates vertical (z) motion into the transducer rotation necessary for data collection in the radii. When coupled with an appropriate data collection and display systems, the present system allows for complete 2-D imaging of the joint interiors over a near 90 degree angle. Because it takes a sweep of the radius, the device collects more data than hand-held UT inspection (limited by the angles the operator selects) and multiple channel and transducer UT inspection (limited by the pre-set angle of each transducer). Without the present fixture for automated ultrasonic scanning, the programming of an expensive multi-axis robot (with rotational axis capability) would be required to obtain a comparable data set.

What is claimed is:

1. An inspection system for ultrasonic scanning or radii in a structure comprising in combination:
    an assembly having two arms containing bushings that slide on rods for holding the assembly together;
    an elastic band for pulling said arms toward each other hand holding the arms against the structure to be inspected;
    said arms having fingers holding ultrasonic transducers for rotation;
    said transducers electrically coupled to a pulse receiver;
    a signal processor coupled to said pulse receiver;
    said assembly having a robot including positionally encoded motors for producing x and axis scanning location information relative to said structure;
    said signal processor receiving said z and x axis scanning information relative to said structure; and
    means for combining the return pulses features with the encoder position to produce two-dimensional images of ultrasonic data for evaluation on a cathode ray tube display.

2. A fixture for automatic ultrasonic scanning of an aerospace structure comprising in combination:
    two arms containing bushings which slide on rods;
    an elastic band for pulling said arms towards each other and holding said arms against a part to be inspected;
    said arms having fingers holding ultrasonic transducers for rotation; and wherein;
        the orientation of said fingers is controlled by the vertical (z-axis) motion of said fixture relative to said aerospace structure.

* * * * *